(12) United States Patent
Chau et al.

(10) Patent No.: US 6,818,333 B2
(45) Date of Patent: Nov. 16, 2004

(54) THIN ZEOLITE MEMBRANE, ITS PREPARATION AND ITS USE IN SEPARATION

(75) Inventors: Christophe Chau, Rueil Malmaison (FR); Mickaël Sicard, Palaiseau (FR); Ronan Le Dred, Riedisheim (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 10/452,940

(22) Filed: Jun. 3, 2003

(65) Prior Publication Data

US 2004/0033370 A1 Feb. 19, 2004

(30) Foreign Application Priority Data

Jun. 3, 2002 (FR) .............................. 02 06818
Jun. 3, 2002 (FR) .............................. 02 06817

(51) Int. Cl.⁷ .................... B32B 17/00; B01J 20/28; B01J 29/06
(52) U.S. Cl. .................. 428/702; 428/446; 428/426; 428/701; 428/304.4; 428/307.3; 502/4; 502/64; 502/70; 210/651; 210/653; 210/500.21; 95/45; 95/902; 264/45.1; 264/45.5; 423/700
(58) Field of Search .................. 502/4, 64, 70; 210/651, 653, 500.21; 95/45, 902; 264/45.1, 45.5; 423/700; 428/446, 426, 304.4, 307.3, 702, 701

(56) References Cited

U.S. PATENT DOCUMENTS 5,464,798 A * 11/1995 Jia et al. ................... 502/64
6,140,263 A   10/2000 Anstett et al.
6,197,427 B1   3/2001 Anstett et al.

FOREIGN PATENT DOCUMENTS

EP   0808655        11/1997
WO   WO 00/53297    9/2000

OTHER PUBLICATIONS

Z.A.E.P Vroon et al "Transport Properties of Alkanes Through Ceramic Thin Zeolite MFI Membranes", Journal of Membrane Science, vol. 113, 1996, p. 293–300 XP004041576.

K. Kusakabe et al. "Morphology and Gas Permeance of ZSM–5–Type Zeolite Membrane Formed on a Porous Alpha–Alumina Support Tube", Journal of Membrane Science, vol. 116, 1996, p. 39–46 XP004041537.

* cited by examiner

*Primary Examiner*—Deborah Jones
*Assistant Examiner*—Ling Xu
(74) *Attorney, Agent, or Firm*—Millen, White, Zelano & Branigan, P.C.

(57) ABSTRACT

Described is a supported zeolite membrane that consists of a zeolite/substrate composite layer that exhibits, in the n-butane/isobutane separation, a permeance of n-butane of at least $6.10^{-7}$ mol/m².s.Pa and a selectivity of at least 250 at the temperature of 180° C. Said zeolite/substrate composite layer is thin and continuous. This membrane is used in processes for gas separation, vapor separation and liquid separation.

18 Claims, No Drawings

THIN ZEOLITE MEMBRANE, ITS PREPARATION AND ITS USE IN SEPARATION

This application relates to Applicants' concurrently filed application application Ser. No. 10/453,867 entitled "Process For The Preparation Of A Thin Zeolite Membrane".

This invention relates to the field of supported zeolite membranes that are used in separation.

More particularly, it has as its object a supported zeolite membrane, a process for its preparation and its use in separation.

Various processes for developing zeolite membranes have already been described. To date, it appears difficult to obtain in a controlled and reproducible manner zeolite membranes whose layer that contains the zeolite is continuous and thin. The thinness and the continuity of such a layer are essential parameters for obtaining a membrane material that exhibits advantageous properties that can be used in industrial separation processes. In particular, it is particularly difficult to control the preparation of zeolite membranes: the production processes involve several stages, and it is often necessary to reproduce the crystallization stage on several occasions to obtain, following stages that are time-intensive, high in operating costs, chemical products and energy, a continuous layer that can be used in separation. Furthermore, the thermal and mechanical stability of these inorganic membranes is crucial. Actually, the inorganic materials can in general be used at relatively high temperatures, for example higher than the organic polymer membranes that generally operate at a temperature of less than 100° C. It is then essential, for an industrial and commercial application, to use a membrane that can remain stable during operations and uses at high temperatures, and even high pressures. The hydrothermal path that involves porous substrates exhibits the advantage of stabilizing the zeolite crystals in the pores of a porous matrix (alumina, stainless steel, for example) and also on the surface of the latter.

In Patent Application EP-A-0 778 075, a process for developing zeolite membranes that are supported by porous glass is described. Patent U.S. Pat. No. 5,429,743 and International Patent Application WO-A-95/29751 describe operating procedures for obtaining composite membranes that are supported by an inorganic macroporous matrix. Reference can also be made to documents U.S. Pat. No. 4,099,692, WO-A-93/19840, U.S. Pat. No. 5,567,664 and WO-A-96/01683. In International Patent Application WO-A-00/33948, a process for obtaining composite membranes of zeolite supported on optionally multi-channel tubular solids is described. All of these composite membrane materials with a zeolite base are formed by a zeolite phase that is deposited on a substrate. A series of recent patents (U.S. Pat. Nos. 5,871,650, 5,968,366, 6,090,289, 6,074,457, WO-A-00/53297, and WO-A-00/53298) describes the preparation of membranes whose MFI zeolite phase is found on the outside surface of a porous substrate. The crystallization of the zeolite is generally carried out by multiple hydrothermal treatments of a mixture that contains the precursors of the zeolite phase, which increases the effective thickness of the separating layer. When the crystallization stage of the zeolite is reproduced on several occasions, the synthesis is reproduced after an optional return of the material to ambient temperature, washing and drying of said material.

The repetition and the succession of identical operations for the preparation of zeolite membranes allow the deposition of successive layers and/or the formation of zeolite crystals that fill the interparticulate spaces, which allows the production of a continuous layer for the separation. This method of synthesis in several stages, if it leads to the production of a continuous layer, also leads to the production of thick zeolite layers that run the risk of cracking during the calcination of the membrane (Vroon, Z. A. E. P., Keizer, K., Burggraaf, A. J., Verweij, H., J. Membr. Sci. 144 (1998) 65–76) from bringing the membrane separation unit into steady operation or from use at high temperature. Furthermore, the increase in thickness can considerably limit the transfer of material through the membrane during the separation operation and thus can reduce the technical and economic advantage of the membrane separation operation, due to a reduction in productivity of said separation stage. In addition, a membrane whose separating layer is thick will require using large surface areas of said membrane material to treat a flow of feedstock of the mixture to be separated, which is reflected by high investments. In addition, this method of synthesis in several stages requires a large amount of precursors of the zeolite phase, which increases in particular the cost of raw materials and precursors used. It also exhibits the drawback of extending the period for obtaining the membrane material and increasing the operating cost of the separation.

One of the difficulties linked to the preparation of zeolite-based membranes resides in particular in the monitoring of the crystallization of the zeolite so as to obtain zeolite crystals that are well linked to the substrate, located primarily in the pores of the substrate, thus forming a continuous and thin zeolite/substrate composite layer (obtained by obstructing the empty voids of the substrate by zeolite phase crystals) so as to limit the resistance of transfer through the membrane material. Placing most, and preferably all, of the zeolite phase in the pores of the substrate imparts very good thermal and mechanical resistance to the membrane material. It cannot be ruled out, however, that a minority portion of the zeolite phase be located on the outside surface of the substrate.

One of the essential objects of this invention is to provide a supported zeolite membrane in which the zeolite phase, crystallized by a single hydrothermal treatment, exhibits the characteristics set forth above. In particular, said zeolite phase, which is active in separation, i.e., selective compared to the compounds to be separated, is thin and also exhibits a very high crystallinity.

The supported zeolite membrane according to the invention comprises a zeolite/substrate composite layer and is characterized in that it exhibits, in the n-butane/isobutane separation, a permeance of n-butane of at least $6.10^{-7}$ mol/m$^2$.s.Pa and a selectivity of at least 250 at the temperature of 180° C.

Recall that the permeance of a gas, expressed in mol/m$^2$.s.Pa, is, by definition, the molar flow rate (mol/s) of this gas related to the unit membrane surface area (m$^2$) and related to the partial-pressure difference of this gas between the upstream (where the feedstock circulates) and the downstream (where the permeate is recovered). The permeance of a gas is therefore the molar flow rate of this gas that passes through the membrane per unit of surface area and pressure. Selectivity α (called permselectivity) is, in the case of measurements of permeation of pure elements, the ratio of the permeances of these pure elements. Within the scope of this invention, the selectivity is therefore the ratio of the permeances of n-butane and isobutane.

The supported zeolite membrane according to the invention preferably exhibits, in the n-butane/isobutane separation, a permeance of n-butane of at least $8.10^{-7}$ mol/m².s.Pa and very preferably at least $10.10^{-7}$ mol/m².s.Pa at the temperature of 180° C. The high permeance of n-butane of the membranes according to the invention demonstrates the small thickness of the zeolite phase as well as that of the zeolite/substrate composite layer that exhibits a thickness that is less than 2 μm and preferably less than 1 μm and very preferably less than 0.5 μm.

The permeance is measured as follows: the membrane is inserted in a permeating device (permeation measurement module) with carbon joints that keep the measurement module sealed. The unit (module/membrane) is placed in a gaseous permeation unit, and the material is treated in advance at 350° C. under a flow of cover gas, such as helium, that makes it possible to eliminate all traces of adsorbable gas on the outside surface and in the inside pores of the membrane material. During the gas permeation measurements, the membrane is subjected to a difference in pressure, the pressure of the upstream side where the feedstock (pure linear butane $n-C_4H_{10}$ or pure isobutane $i-C_4H_{10}$) circulates is kept constant at 1.5 bar (0.15 MPa) absolute, and the pressure of the downstream side, where the permeate is recovered after selective extraction of a portion of the molecules that are present in the feedstock, is the atmospheric pressure. This pressure difference constitutes the driving force of the transfer through the membrane. The gas flow that passes through the membrane is measured with a volumetric flowmeter. The detection threshold is less than 0.002 ml/mn or about $10^{-6}$ mol/m².s of n-butane or isobutane. The measurement of the gas flows passing through the membrane is carried out with pure n-butane and isobutane. During the gas permeation measurements, the temperature is kept at 180° C.

It should be noted that with the selection of these sampler molecules that are n-butane and isobutane, this method of characterization is considered to be a very strict and very selective criterion for characterizing microporous inorganic membranes and in particular zeolite membranes. It consequently allows the demonstration of the presence of any discontinuity, defects, or cracks in the zeolite/substrate composite layer. Conversely, the absence of significant defects in the membrane reveals a very high separation potential. In particular, this characterization method that uses n-butane and isobutane is very strict relative to other characterization tests that are used in the prior art, for example the tests using the pairs $N_2/SF_6$, $H_2/n-C_4$ or $H_2/i-C_4$.

The supported zeolite membrane according to the invention preferably exhibits a selectivity of at least 1,000.

The supported zeolite membrane according to the invention comprises a continuous and thin zeolite/substrate composite layer whose zeolite phase is also thin, which is reflected by very high separation performance levels, in particular by a very high selectivity or separating power of the membrane, i.e., at least 250, preferably at least 1,000, and even infinite. Said zeolite/substrate composite layer is active in separation, i.e., selective compared to compounds to be separated. Furthermore, the membranes according to the invention are composite materials, whose selective layer or separating layer is formed by zeolite crystals that are immobilized and stabilized in the pores of an inorganic substrate. The zeolite phase is for the most part, preferably completely, located in the pores of the substrate, which imparts a very good thermal and mechanical resistance to the membrane material. This zeolite phase exhibits a very high crystallinity, preferably at least 85% and very preferably at least 90%. The zeolite membranes according to the invention also exhibit a very good structural integrity, i.e., an absence of defects in the structure of the zeolite/substrate composite layer and an absence of interparticulate spaces, i.e., voids that are present between the crystals of the zeolite, which is difficult to obtain by the prior processes in a single stage. The thinness of the zeolite layer does not prevent it from advantageously using the membrane according to the invention at high temperatures, in particular higher than 100° C. (such as, for example 180° C.).

The zeolite phase that is contained in said composite layer is preferably of MFI-structural type (silicalite-1 or ZSM-5) with channel dimensions of 0.51*0.55 and 0.53*0.56 nm².

The substrate that is included in the zeolite/substrate composite layer of the membrane according to the invention consists of a porous inorganic material. A ceramic substrate with an alumina and/or zirconia and/or titanium oxide base is a suitable substrate. Other materials, of the following types, may also be suitable: carbon, silica, zeolites, clays, porous glass, and porous metal. The use of an alumina substrate of the alpha- or gamma-allotropic variety is preferred. This substrate may come in, for example, flat form or tubular form or in the form of hollow fibers or else multichannel monoliths. Other geometries may be suitable, but the substrate geometries that are compatible with an industrial use of these membranes are advantageously used. In particular, the tubular substrates and the substrates in the form of hollow fibers can operate modules and compact units (high ratio of membrane surface area/equipment volume) to process significant feedstock flow rates.

This invention also relates to a process for controlled development of zeolite membranes according to the invention.

The supported zeolite membranes according to the invention are advantageously prepared by a process that comprises:

a) the formation of a gel or a solution that comprises at least one source of silica and water, supplemented with at least one polar organic compound;

b) bringing into contact said gel or said solution with a porous substrate;

c) the crystallization of the zeolite starting from said gel or said solution; and d) the elimination of residual agents.

The silica source that is used in stage (a) of the process is preferably a colloidal silica or a precipitated silica. These can also be silicate ions such as sodium silicate, silicon alkoxides or silicon tetrachloride.

Other elements can also be introduced in a minority amount during stage (a) of the process according to the invention. In particular, aluminum, boron, gallium, titanium, germanium, and phosphorus as well as the mixture of these elements can be added during stage (a).

The polar organic compound that is supplemented with gel or the solution that comprises at least said source of silica and water is preferably a basic compound. These are advantageously organic hydroxides, such as tetrapropylammonium hydroxide, organic structuring agents that contain ionic pairs (ammonium or phosphonium ions and the corresponding anions) or neutral molecules (amines, alcohols or ethers such as crown ethers and cryptands). The molar ratio of the polar organic compound to the silica is between 0.3:1 and 0.6:1 and preferably between 0.35:1 and 0.50:1. The hydroxide ions or fluoride ions can be used, furthermore, for the dissolution of the precursors and are introduced into the preparation medium, for example, in the form of sodium hydroxide, organic hydroxides and hydrofluoric acid.

The dilution of the silica source in the solution or the gel that is used in stage (a) and the crystallization time of the zeolite in stage (c) are essential parameters to be controlled to attain the desired properties of the zeolite phase that is deposited in the pores of the substrate.

A particular embodiment of the process according to the invention consists in using a precipitated silica as a silica source in stage (a), in a molar ratio of the water to the silica of between 45:1 and 65:1 and to apply in stage (c) a crystallization time that is less than or equal to 80 hours.

Another particular embodiment of the process according to the invention consists in using a colloidal silica as a silica source in stage (a), in a molar ratio of water to silica of between 18:1 and 35:1 and to apply in stage (c) a crystallization time that is less than or equal to 45 hours.

According to the invention, the crystallization of the zeolite in stage (c) of the process according to the invention is carried out in a single step, i.e., the zeolite is crystallized by a single hydrothermal treatment.

The elimination of residual agents, primarily of the polar organic compound, according to stage (d) of the process according to the invention, is carried out by thermal treatment that takes place between 350 and 550° C., preferably between 400° C. and 500° C., in a furnace under an atmosphere of air or under an $N_2/O_2$ atmosphere in variable proportions. After these residual agents are eliminated, the micropores of the zeolite membranes can then be used for a separation operation. The high-temperature calcination, i.e., carried out between 350 and 550° C., preferably between 400° C. and 500° C., of the membrane so as to eliminate the residual agents has no influence on the separating performance levels of the membrane, which remain very satisfactory. This very good thermal resistance of the membrane is advantageously used to carry out high-temperature separations in fields where the organic membrane operations cannot be carried out because of their low thermal resistance. The zeolite membranes according to the invention therefore seem particularly suited for both high-temperature and low-temperature separations in industrial processes that make it necessary to process sometimes large amounts of feedstock while limiting the investment required (high-permeability membranes).

The zeolite membranes according to the invention can also be used for different molecular separations. They are advantageously used in gas separation processes, vapor separation processes or liquid separation processes. They thus are preferably used for separating:

- linear and branched paraffins (n- and iso-paraffins), such as, for example, n-butane and isobutane,
- paraffins that are branched among them (mono-branched and di-branched or multi-branched),
- linear and branched olefins (n- and iso-olefins),
- paraffins and olefins,
- naphthenes and paraffins,
- paraffins and aromatic compounds,
- hydrogen and hydrocarbons; for example in mixtures that contain the hydrogen and hydrocarbons below, present separately or simultaneously, light paraffins such as methane, ethane, propane or butane and isobutane; or else hydrogen, and light olefins such as ethylene, propylene and isomers of butenes, isobutene; or else hydrogen and polyunsaturated hydrocarbons such as acetylene, propyne, butyne and butadiene, whereby these hydrocarbons are taken separately with hydrogen or in a mixture,
- isomers of xylene (ortho-, meta-, and para-xylenes),
- methane and $CO_2$.

According to the invention, the quality and the properties of molecular sieving of the zeolite phase are used to separate molecules whose dimensions are strictly less than, on the one hand, and strictly larger than, on the other hand, those of the pores of the zeolite (separation by size differentiation). By way of illustration, in the case of the MFI zeolite that has a mean pore size of 0.55 nm (channel dimensions of 0.51*0.55 and 0.53*0.56 $nm^2$), the zeolite membranes according to the invention can be used for the separation of molecules, in particular containing carbon and hydrogen atoms, whose dimensions are, on the one hand, less than approximately 0.45 nm and, on the other hand, larger than 0.55 nm. Furthermore, the interactions between the molecules to be separated and the zeolite phase of the membrane can also be used to carry out the separation of said molecules (separation by adsorption).

The following examples illustrate the invention and should in no way be considered as limiting.

EXAMPLE 1

Preparation of a Zeolite Membrane (According to the Invention)

A zeolite precursor solution is prepared from a silica source (Aerosil 380® with a specific surface area that is equal to 380 $m^2/g$ that is marketed by the Degussa Company), mixed at ambient temperature with distilled water and a molar aqueous solution of the polar organic agent of tetrapropyl ammonium hydroxide TPAOH (Fluka). The resulting solution allows per molar composition: 1 $SiO_2$: 0.4 TPAOH: 63.7 $H_2O$. This solution is allowed to mature while being stirred vigorously for 72 hours, which allows a partial depolymerization and a reorganization of the silica into silicate radicals that are more reactive than the original source. A partial gelling of the precursors may occur, whereby the solution is more or less clear. An alpha-alumina porous substrate (marketed by the Exekia Company), previously washed with distilled water and then dried at 60° C., is then immersed in the previously-prepared solution. All of the precursors and the porous substrate are placed in a sealed autoclave, inserted into a furnace that is kept at 175° C. for 60 hours. After returning to ambient temperature, the membrane is collected and washed with distilled water and then dried at 60° C. The elimination of residual agents, primarily the tetrapropyl ammonium hydroxide TPAOH, is carried out by thermal treatment at 480° C. in a furnace under an atmosphere of air. After these residual agents are eliminated, the micropores of the zeolite membranes can then be used for a separation operation. The phase analysis by x-ray diffraction on this membrane that is obtained after 60 hours of dwell time in an autoclave confirms the presence of MFI zeolite crystals that are located in the pores of the alpha-alumina substrate.

EXAMPLE 2

Preparation of a Zeolite Membrane (According to the Invention)

The preparation procedure is analogous to the one that is described in Example 1, but the preparation is conducted in the presence of a colloidal silica source, Bindzil 40/130® (marketed by the Akzo Nobel Company). The preparation of a zeolite membrane is thus initiated for which the precursor solution of the MFI zeolite respectively allows 1 $SiO_2$: 0.4

TPAOH: 18.3 $H_2O$ for molar stoichiometry. The crystallization time is 30 hours. The elimination of the residual agents, primarily the tetrapropyl ammonium hydroxide TPAOH, is carried out by thermal treatment at 480° C. in a furnace under an atmosphere of air. After these residual agents are eliminated, the micropores of the zeolite membranes can then be used for a separation operation. The phase analysis by x-ray diffraction on this membrane that is obtained after 30 hours of dwell time in an autoclave confirms the presence of MFI zeolite crystals that are located in the pores of the alpha-alumina substrate.

EXAMPLE 3

Preparation of Zeolite Membranes (Not in Accordance with the Invention)

a) Use of a Precipitated Silica Source

The operating procedure that is described in Example 1 is adopted, modifying only the amount of water that is introduced into the solution, precursor of the MFI zeolite and the crystallization time. The silica source is Aerosil 380®. The crystallization time is 72 hours, and the elimination of the tetrapropyl ammonium hydroxide TPAOH is carried out at 480° C.

The preparation of a zeolite membrane is thus initiated for which the precursor solution of the MFI zeolite respectively allows 1 $SiO_2$: 0.4 TPAOH: 29.6 $H_2O$ for molar stoichiometry. The phase analysis by x-ray diffraction on this membrane that is obtained after 72 hours of dwell time in an autoclave confirms the presence of MFI zeolite crystals that are located in the pores of the alpha-alumina substrate.

b) Use of a Colloidal Silica Source

The operating procedure that is described in Example 2 is adopted, modifying only the crystallization time. The silica source is Bindzil 40/130®. The crystallization time is 72 hours, and the elimination of the tetrapropyl ammonium hydroxide TPAOH is carried out at 480° C.

The preparation of a zeolite membrane is thus initiated for which the precursor solution of the MFI zeolite respectively allows 1 $SiO_2$: 0.4 TPAOH: 18.3 $H_2O$ for molar stoichiometry. The phase analysis by x-ray diffraction on this membrane that is obtained after 72 hours of dwell time in an autoclave confirms the presence of MFI zeolite crystals that are located in the pores of the alpha-alumina substrate.

EXAMPLE 4

Separation Performance Levels of Zeolite Membrane Materials (According to the Invention)

Five membranes (A, B, C, D, E) are prepared according to the method of synthesis that is described in Example 1. Membrane E is obtained according to the method of synthesis described in Example 1 but with a crystallization time of 72 hours.

The performance levels of an F membrane prepared according to the method of synthesis described in Example 2 are also tested.

The performance levels of membranes A, B, C, D, E, and F according to the invention are demonstrated by gas separation measurement (gaseous permeation), carried out by using n-butane and isobutane according to the above-described procedure in the description.

The results are summarized in Table 1.

TABLE 1

Characterization of the Performance Levels of Zeolite Membranes According to the Invention at 180° C.

| Membrane | $nC_4H_{10}$ Permeance ($10^{-7}$ mol/m².s.Pa) | $iC_4H_{10}$ Permeance ($10^{-7}$ mol/m².s.Pa) | Selectivity of $nC_4H_{10}/iC_4H_{10}$ |
|---|---|---|---|
| A | 11.62 | 0.000 | Infinite |
| B | 16.91 | 0.042 | 400 |
| C | 17.16 | 0.061 | 282 |
| D | 20.95 | 0.000 | Infinite |
| E | 7.10 | 0.000 | Infinite |
| F | 9.66 | 0.000 | Infinite |

The zeolite membranes according to the invention exhibit, at the end of the characterization measurements, very high permeances, most greater than $10.10^{-7}$ mol/m².s.Pa of n-butane at the temperature of 180° C., which reflects a very small thickness of zeolite membranes A, B, C, D, E and F. Under the same conditions, these materials are impermeable to isobutane (A, D, E, F) or their permeances are very low (B and C), in all cases less than $0.065.10^{-7}$ mol/m².s.Pa of isobutane. As a result, the n-butane/isobutane selectivity or $nC_4H_{10}/iC_4H_{10}$ reaches particularly high values, in all cases greater than 250, and the separation is particularly effective, which demonstrates the continuity of the zeolite/substrate composite layer of each of the membranes according to the invention. This layer is selective for separating isomers from hydrocarbons whose dimensions differ by only 0.6 nanometer (kinetic diameter of 0.43 nm for n-butane and 0.49 nm for isobutane). By comparison, it is generally accepted in literature that the MFI-structural-type zeolite membranes exhibit a good textural integrity, i.e., an absence of mesopore- and macropore-type structural defects, when the n-butane/isobutane selectivity is greater than 10 (Vroon et al., J. Membr. Sci. 113 (1996) 293).

EXAMPLE 5

Separating Performance Levels of Zeolite Membrane Materials (Not in Accordance with the Invention)

The membrane that is prepared according to Example 3a (membrane G) and the one that is prepared according to Example 3b (membrane H) are subjected to the same test of performance levels (gaseous permeation) as the membranes according to the invention that are prepared according to Examples 1 and 2. The conditions for carrying out the gaseous permeation with $n-C_4$ and $iC_4$ are similar to the ones that are explained above in the description.

The results are summarized in Table 2.

TABLE 2

Characterization of the Performance Levels of Zeolite Membranes G and H at 180° C.

| Membrane | $nC_4H_{10}$ Permeance ($10^{-7}$ mol/m².s.Pa) | $iC_4H_{10}$ Permeance ($10^{-7}$ mol/m².s.Pa) | Selectivity of $nC_4H_{10}/iC_4H_{10}$ |
|---|---|---|---|
| G | 3.18 | 0.000 | Infinite |
| H | 1.84 | 0.000 | Infinite |

In the n-C4/i-C4 separation, membranes G and H exhibit n-butane permeances that are much lower than those of the membranes according to the invention. The membranes according to the invention actually exhibit an n-butane permeance that is about 2 to 11× higher than that of the membranes that are not in accordance with the invention, while preserving high, and even infinite, selectivities. In other words, the membranes according to the invention contain a zeolite/substrate composite layer that can be up to at least 11× thinner than that of the membranes that are not in accordance with the invention.

The preceding examples can be repeated with similar success by substituting the generically or specifically described reactants and/or operating conditions of this invention for those used in the preceding examples.

The entire disclosures of all applications, patents and publications, cited herein and of corresponding application Ser. No. 02/06.817, filed Jun. 3, 2002 is incorporated by reference herein.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. Supported zeolite membrane that consists of a zeolite/substrate composite layer, characterized in that it exhibits, in the n-butane/isobutane separation, an n-butane permeance of at least $6.10^{-7}$ mol/m$^2$.s.Pa and a selectivity of at least 250 at the temperature of 180° C.

2. Supported zeolite membrane according to claim 1, wherein it exhibits, in the n-butane/isobutane separation, an n-butane permeance of at least $8.10^{-7}$ mol/m$^2$.s.Pa at the temperature of 180° C.

3. Supported zeolite membrane according to claim 2, wherein it exhibits, in the n-butane/isobutane separation, an n-butane permeance of at least $10.10^{-7}$ mol/m$^2$.s.Pa at the temperature of 180° C.

4. Supported zeolite membrane according to one of claims 1 to 3, wherein it exhibits a selectivity of at least 1,000.

5. Supported zeolite membrane according to one of claims 1 to 4, wherein the zeolite phase that is contained in said composite layer is of the MFI-structural type.

6. Supported zeolite membrane according to one of claims 1 to 5, wherein the substrate is selected from among the following materials: ceramic based on alumina and/or zirconia and/or titanium oxide, carbon, silica, zeolites, clays, porous glass and porous metal.

7. Process for the preparation of a supported zeolite membrane according to one of claims 1 to 6, comprising:

a) the formation of a gel or a solution that comprises a source of silica and water, supplemented with at least one polar organic compound;

b) bringing into contact said gel or said solution with a porous substrate;

c) the crystallization of the zeolite starting from said gel or said solution; and d) the elimination of residual agents.

8. Process for the preparation of a supported zeolite membrane according to claim 7, wherein in said stage a), the silica source is a precipitated silica and the molar ratio of the water to the silica is between 45:1 and 65:1 and wherein in stage c), the crystallization time is less than or equal to 80 hours.

9. Process for the preparation of a supported zeolite membrane according to claim 7, wherein in said stage a), the silica source is a colloidal silica and the molar ratio of the water to the silica is between 18:1 and 35:1 and wherein in stage c), the crystallization time is less than or equal to 45 hours.

10. Use of a membrane according to one of claims 1 to 6 in a process for gas separation, vapor separation or liquid separation.

11. Use of a membrane according to one of claims 1 to 6 for the separation of linear and branched paraffins.

12. Use of a membrane according to one of claims 1 to 6 for the separation of linear and branched olefins.

13. Use of a membrane according to one of claims 1 to 6 for the separation of paraffins and olefins.

14. Use of a membrane according to one of claims 1 to 6 for the separation of naphthenes and paraffins.

15. Use of a membrane according to one of claims 1 to 6 for the separation of paraffins and aromatic compounds.

16. Use of a membrane according to one of claims 1 to 6 for the separation of hydrogen and hydrocarbons.

17. Use of a membrane according to one of claims 1 to 6 for the separation of isomers from xylenes.

18. Use of a membrane according to one of claims 1 to 6 for the separation of methane and $CO_2$.

* * * * *

UNITED STATES PATENT AND TRADEMARK OFFICE
CERTIFICATE OF CORRECTION

PATENT NO. : 6,818,333 B2
DATED : November 16, 2004
INVENTOR(S) : Christophe Chau et al.

It is certified that error appears in the above-identified patent and that said Letters Patent is hereby corrected as shown below:

Column 9,
Line 23, delete "Supported" and insert -- A supported --.
Line 23, delete "that consists of" and insert -- comprising --.
Line 27, delete "the" and insert -- a --.
Line 28, delete "Supported" and insert -- A supported --.
Line 31, delete "Supported" and insert -- A supported --.
Line 36, delete "Supported" and insert -- A supported --.
Lines 36-37, delete "one of claims 1 to 3" and insert -- claim 1 --.
Line 38, delete "Supported" and insert -- A supported --.
Lines 38-39, delete, "one of claims 1 to 4" and insert -- claim 1 --.
Line 41, delete "Supported" and insert -- A supported --.
Lines 41-42, delete "one of claims 1 to 5" and Insert -- claim 1 --.
Lines 42-43, delete "among the following materials" and insert -- the group consisting of --.

Column 10,
Line 1, delete "Process" and insert -- A process --.
Line 2, delete "one of claims 1 to 6" and insert -- claim 1 --.
Line 13, delete "Process" and insert -- A process --.
Line 19, delete "Process" and insert -- A process --.

Column 11,
Line 24, delete "Use of a membrane according to one of claims 1 to 6 in a process for" and insert -- In a process comprising separating a fluid through a membrane by --.
Line 26, after "separation" insert -- , the improvement wherein the membrane is according to claim 1 --.
Line 27, delete "Use of a membrane according to one of claims 1 to 6" and insert -- A process according to claim 10 --.
Claim 12, Cancelled
Line 32, delete "Use of a membrane according to one of claims 1 to 6" and insert -- A process according to claim 10 --.
Line 34, delete "Use of a membrane according to one of claims 1 to 6" and insert -- A process according to claim 10 --.
Line 36, delete "Use of a membrane according to one of claims 1 to 6" and insert -- A process according to claim 10 --.
Line 38, delete "Use of a membrane according to one of claims 1 to 6" and insert -- A process according to claim 10 --.
Line 40, delete "Use of a membrane according to one of claims 1 to 6" and insert -- A process according to claim 10 --.
Line 42, delete "Use of a membrane according to one of claims 1 to 6" and insert -- A process according to claim 10 --.

UNITED STATES PATENT AND TRADEMARK OFFICE
CERTIFICATE OF CORRECTION

PATENT NO. : 6,818,333 B2
DATED : November 16, 2004
INVENTOR(S) : Christophe Chau et al.

It is certified that error appears in the above-identified patent and that said Letters Patent is hereby corrected as shown below:

Column 10, (cont.)
Line 44, delete "Use of a membrane according to one of claims 1 to 6" and insert
-- A process according to claim 10 --.

Signed and Sealed this

Twenty-eighth Day of June, 2005

JON W. DUDAS
*Director of the United States Patent and Trademark Office*